United States Patent
Ebadollahi et al.

(10) Patent No.: US 8,660,857 B2
(45) Date of Patent: Feb. 25, 2014

(54) METHOD AND SYSTEM FOR OUTCOME BASED REFERRAL USING HEALTHCARE DATA OF PATIENT AND PHYSICIAN POPULATIONS

(75) Inventors: Shahram Ebadollahi, White Plains, NY (US); Jianying Hu, Bronx, NY (US); Martin S. Kohn, East Hills, NY (US); Jonathan D. Laserson, Menlo Park, CA (US); Hani Neuvirth-Telem, Tel Aviv (IL); Lavi Shpigelman, Jerusalem (IL); Robert K. Sorrentino, Rancho Palos Verdes, CA (US)

(73) Assignee: International Business Machines Corporation, Armonk, NY (US)

( * ) Notice: Subject to any disclaimer, the term of this patent is extended or adjusted under 35 U.S.C. 154(b) by 182 days.

(21) Appl. No.: 12/913,042

(22) Filed: Oct. 27, 2010

(65) Prior Publication Data

US 2012/0109683 A1  May 3, 2012

(51) Int. Cl.
*G06Q 50/00* (2012.01)
*G06Q 10/00* (2012.01)

(52) U.S. Cl.
USPC .................................................. 705/2; 705/3

(58) Field of Classification Search
USPC ................................................................ 705/2
See application file for complete search history.

(56) References Cited

U.S. PATENT DOCUMENTS

| | | | |
|---|---|---|---|
| 5,301,105 A | 4/1994 | Cummings, Jr. | |
| 6,256,613 B1 | 7/2001 | Falchuk et al. | |
| 7,065,528 B2 | 6/2006 | Herz et al. | |
| 7,558,738 B1 | 7/2009 | Flatt | |
| 2006/0106644 A1 | 5/2006 | Koo et al. | |
| 2008/0010087 A1 | 1/2008 | Daniel et al. | |
| 2008/0133290 A1* | 6/2008 | Siegrist et al. | 705/7 |

OTHER PUBLICATIONS

Chilingerian, Evaluating physician efficiencyin hospitals:A multivariate analysis of bestpractices, 1995, European Journal of Operational Research 80, No. 3, p. 548-574.*
Pope, G., et al. "Risk Adjustment of Medicare Capitation Payments Using the CMS-HCC Model" Health Care Financing Review. vol. 25, No. 4. Summer 2004. pp. 119-141.
Rosen-Zvi, M., et al. "Selecting Anti-HIV Therapies Based on a Variety of Genomic and Clinical Factors" Proceedings 16th International Conference on Intelligent Systems for Molecular Biology (ISMB). Jul. 2008. pp. 399-406.
Sun, J., et al. "Localized Supervised Metric Learning on Temporal Physiological Data" 20th International Conference on Pattern Recognition, ICPR 2010. Aug. 2010. (4 Pages).

* cited by examiner

*Primary Examiner* — Tran Nguyen
(74) *Attorney, Agent, or Firm* — Tutunjian & Bitetto, P.C.; Louis Percello

(57) ABSTRACT

A recommendation system and method includes extracting patient features for a current patient to generate representation of the current patient. The patient features for the current patient are compared to physician features of one or more physicians and patient-to-physician features of a group of patients from medically related records. Outcome measures associated with physicians are compared related to a current query. A future outcome for patient, physician pairs are predicted for the current patient based upon at least one predictive model constructed from the features and outcome measures to output.

25 Claims, 3 Drawing Sheets ly to provide care for a specific medical condition or a set of medical conditions. Recommendations for physicians that are most likely to provide a good outcome for a specific condition or set of conditions for a specific patient would improving care quality and health outcome. In the current healthcare system, physician referral is typically carried out based on the knowledge of a physician currently taking care of the patient, or a health plan that maintains a list of in-network and out-of-network physicians.

METHOD AND SYSTEM FOR OUTCOME BASED REFERRAL USING HEALTHCARE DATA OF PATIENT AND PHYSICIAN POPULATIONS

BACKGROUND

1. Technical Field

The present invention relates to network systems and more particularly to a system and method for healthcare referrals.

2. Description of the Related Art

Physician referral is an important component of the process of clinical care. An objective of referrals is to refer a patient to a physician that is best suited to provide care for a specific medical condition or a set of medical conditions. Recommendations for physicians that are most likely to provide a good outcome for a specific condition or set of conditions for a specific patient would improving care quality and health outcome. In the current healthcare system, physician referral is typically carried out based on the knowledge of a physician currently taking care of the patient, or a health plan that maintains a list of in-network and out-of-network physicians.

SUMMARY

A recommendation system and method includes extracting patient features, physician features and patient-to-physician features from medically related records for a current patient, a group of patients and one or more physicians. Outcome measures are computed from health care data related to a group of patients. A predictive model is constructed from the features and outcome measures to predict a future outcome for a patient-physician pair.

A recommendation system and method includes extracting patient features for a current patient to generate representation of the current patient. The patient features for the current patient are compared to physician features of one or more physicians and patient-to-physician features of a group of patients from medically related records. Outcome measures associated with physicians are compared related to a current query. A future outcome for patient, physician pairs are predicted for the current patient based upon at least one predictive model constructed from the features and outcome measures to output.

A system in accordance with the present principles includes a processor, and memory coupled to the processor. The memory stores a patient, physician pair outcome prediction tool. The tool includes an extraction module configured to store patient features, physician features and patient-to-physician features from medically related records for a current patient, a group of patients and one or more physicians; outcome measures stored from health care data related to a current query; and at least one predictive model constructed from the features and outcome measures to predict a future outcome for a patient, physician pair.

These and other features and advantages will become apparent from the following detailed description of illustrative embodiments thereof; which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

Figure 1:
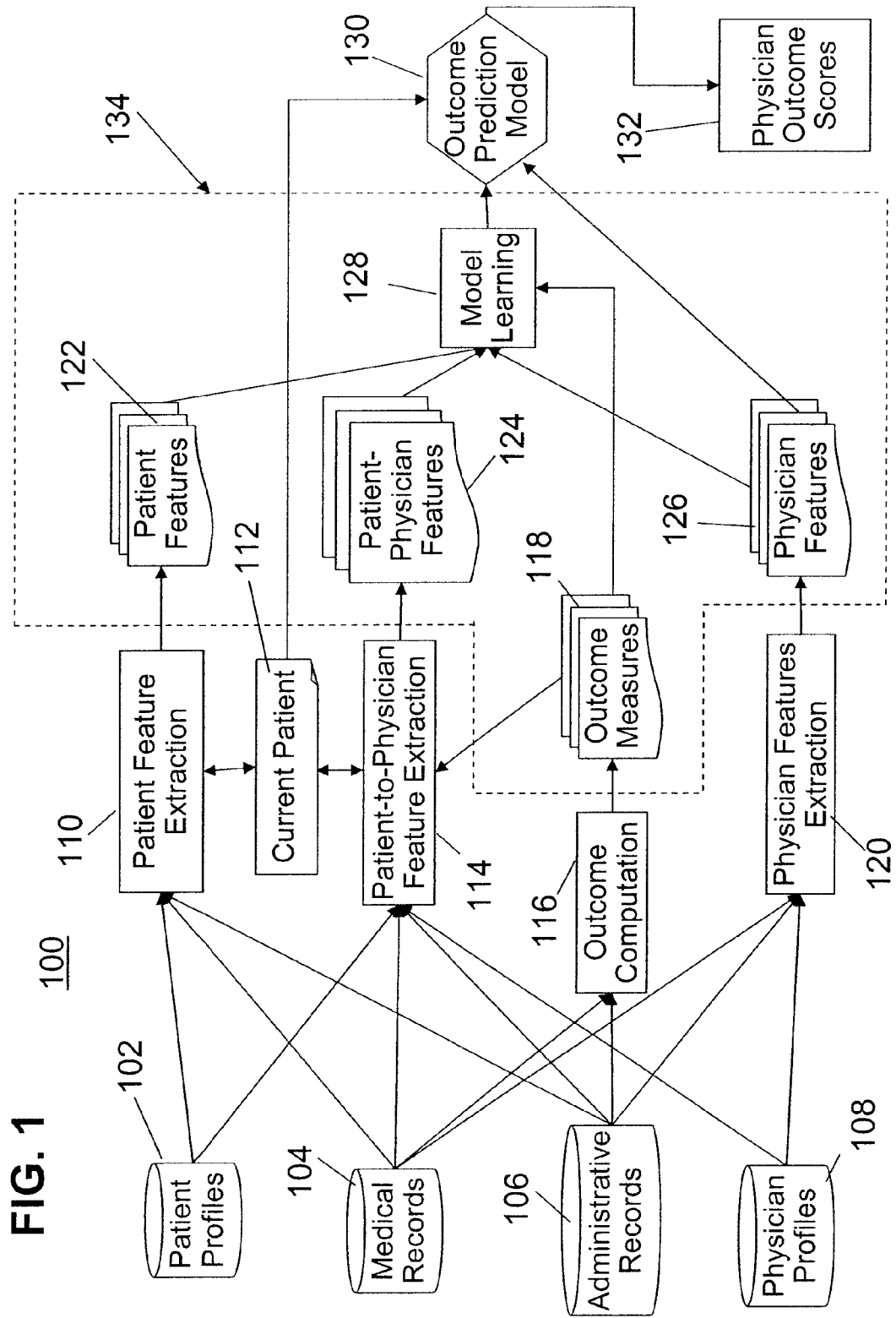
FIG. 1 is a block/flow diagram showing a system/method for generating physician outcome scores for selecting a physician in accordance with one embodiment.

In accordance with the present principles, systems and methods are provided that predict a likely outcome of a (patient, physician) pair using a patient's characteristics, a physician's characteristics and historical patterns of outcome provided by different physicians for related patients. Recommendations are made based on such predictions. The features of the present embodiments can provide important insight into how a given physician is likely to perform for a given patient. One challenge includes that existing medical information systems do not have infrastructure to reliably and efficiently extract patient features and physician features from healthcare administrative records and medical records and to build outcome models using such features.

In one embodiment, the following analytic methods include the following. Patient feature extraction is provided from patient profile records as well as medical records. Physician feature extraction is provided from physician profile records as well as the medical records of patients seen by the physician in the past. Patient-to-physician features capture the similar characteristics between the current patient and patients seen by the physician in the past with both desirable and un-desirable outcomes. A predictive modeling framework can be used to incorporate the above features in advanced predictive modeling methodologies to predict a most-likely outcome of a (patient, physician) pair.

A corresponding system or systems may include a patient feature extraction module that integrates patient related data, extracts patient features, and performs statistical variable selection on these features. A physician feature extraction module integrates physician related data, extracts physician features, and performs statistical variable selection on these features. A patient-to-physician feature extraction module integrates the patient and physician related data, extracts patient-to-physician features, and performs statistical variable selection on these features. An outcome computation module computes outcome measures for specified conditions or combinations of conditions, at both population and individual patient levels. A modeling learning module takes all features and outcome measures and retrospectively constructs models that can be used to predict future outcome for (patient, physician) pair(s). This can be performed during initial training and updated over time. A control module manages feature and model updating either according to pre-defined schedule, or triggered by a specific event.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Referring now to the drawings in which like numerals represent the same or similar elements and initially to FIG. 1, a block/flow diagram showing an illustrative system/method 100 for generating healthcare professional outcome scores based upon patient conditions is provided in accordance with one embodiment. System 100 includes a patient feature extraction module 110 that integrates patient related data from patient profiles 102, medical records 104, administrative records, 106, etc. to extract patient features 122. The patient feature extraction module 110 performs a statistical variable selection on these extracted features. Known variable selection procedures may be employed aimed at selecting a reduced set of the independent variables, i.e., the ones providing a best fit to a model or to a condition or issue at hand.

A physician feature extraction module 120 integrates physician related data, e.g., physician profiles 108, medical records 104, administrative records, 106, etc. to extract physician features 126 and perform statistical variable selection on these features. A patient-to-physician feature extraction module 114 integrates the patient and physician related data (e.g., from physician profiles 108, medical records 104, administrative records, 106, patient profiles 102, etc.), extracts patient-to-physician features 124 and performs statistical variable selection on these features. An outcome computation module 116 computes outcome measures 118 for specified conditions or combinations of conditions, at both population and individual patient levels.

It should be understood that a single extraction module may be employed to perform the extractions of modules 110, 114 and 120. The extraction modules 110, 114 and 120 may be independent as well as illustratively depicted in FIG. 1. It should be further noted that the extractions may be performed in advance to train the system 100 and to generate models based upon available data.

In a training phase of the system 100, a modeling learning module 128 takes all the features and outcome measures and retrospectively constructs models (e.g., outcome prediction model 130) that can be used to predict future outcome for (patient, physician) pair(s). Physician outcome scores 132 may be output from the outcome prediction model 130. A control module 134 manages feature and model updating either according to a predefined schedule, or triggered by a specific event. For example, upon adding a new patient or a new physician model learning module 128 is invoked to outdate any models affected by the new additions.

Patient feature extraction 110 may employ information from many sources. These sources for patient features 122 may include, but are not limited to the following Patient profiles 102 may be employed, which may include basic biographical information such as age, gender, location, preferences, physiological state (e.g., blood pressure, weight, etc.), allergies, etc. Administrative (medical claims) records 106 may be employed, which may include diagnosis codes, procedures codes, insurance provider, etc. Medical records 104 may be employed, which may include lab results, medication records, nursing notes, X-rays, tendencies, trends, samples, patient history, etc. Specific features 122 are defined for each information source to capture salient patient characteristics. The specific features 122 extracted may include such things as the profile information, disease state, medication history, medical procedure history, etc. The disease state may include, e.g., diagnosis, severity measures, groups of co-morbidities, etc. A severity measure is computed using a formula, which may consider, e.g., a number of diagnoses per Clinical Classification System (CCS) mapping code, an aggregated severity score based on Hierarchical Condition Categories (HCC) mapping. Medication history may include generic ingredients, types of medication, days of supply, doses of drugs, etc. Medical procedure history may include procedures undergone, RVU (Relative Value Units), (effort score) of procedures, etc.

Physician feature extraction module 120 functions in the same way as module 110, but extracts different information. The sources for physician features include, but are not restricted to the physician profiles 108. The physician profiles 108 may include specialty, sub-specialty, location, preferences, past performance evaluation scores, etc. Other sources include the administrative 106 and medical records 104 of all patients seen by each physician in the past. Specific features 126 are defined for each information source to capture salient provider characteristics, including the physician's profile, e.g., specialty, sub-specialty, location, location characteristic (i.e., practice size), preferences, past performance evaluation scores, etc.; practice patterns, e.g., medication patterns for sub-populations of patients with certain conditions, procedure patterns for patients with certain conditions, etc.

Patient-to-physician feature extraction module 114 provides patient-physician features 124. The patient-to-physician features 124 are designed to capture the similar characteristics between a current patient 112 and patients seen by the physician in the past with both desirable and un-desirable outcomes from outcome measures 118. For example, if an ailment is chicken pox for a patient, chicken pox related records would be sort after for extractions from physician and patient profiles alike.

For each patient feature or group of features 122, a distance is computed (e.g., outcome measures 118) between the current patient 112 and a group of patients (the patient universe) seen in the past by the same physician, segregated into groups, each with different outcomes. This information is employed in an outcome prediction model 124 to make a determination of a best-suited physician and/or predict a potential outcome of the current patient with one or more different physicians (outcome scores 132).

The patient-to-physician distance metric may be computed as follows. Quantitative measurements of a patient are represented by an N-dimensional feature vector x (e.g., with extracted features). Examples of features are the mean and variance of patient data, counts of different kinds of records etc. A physician is represented by two N-dimensional feature vectors representing centroids of the physician's population of patients with successful and failing treatments (excluding the patient itself). The patient-to-physician distance is a set of two distances to these two centroids. The distance measure can be a standard measure such as Euclidian distance. It could also be a Mahalanobis distance which allows weighting among different features.

In one embodiment, the population centroids computed for each physician can be viewed as an "imaginary representative patient" that received successful or failing treatments from the physician. Then, similarity metrics designed for patient-to-patient distances can be applied to evaluate patient-to-physician distances. One method of learning such a patient-to-patient metric is the Localized Supervised Metric Learning method described in: "Localized Supervised. Metric Learning on Temporal Physical Data", by J. Sun, D. Sow, J. Hu and S. Ebadollahi, in Proc. of $20^{th}$ Int. Conf. on Pattern Recognition, August, 2010. Other metrics may also be employed.

Quantitative measurements of a patient may be represented by an N-dimensional feature vector x (e.g., with the extracted features). Examples of features are the mean and variance of patient data. With this formulation, one goal is to learn a generalized Mahalanobis distance between patient $x_i$ and patient $x_j$ defined as:

$$d_m(x_i, x_j) = \sqrt{(x_i - x_j)^T P (x_i - x_j)} \quad (1)$$

where $P \in \Re^{N \times N}$ is called the precision matrix. Matrix P is positive semi-definite and is used to incorporate the correlations between different feature dimensions. One aspect is to learn the optimal P such that the resulting distance metric has the following properties: 1) Within-class compactness: patients of the same label are close together; and 2) Between-class scatterness: patients of different labels are far away from each other. To formally measure these properties, we use two kinds of neighborhoods: 1) The homogeneous neighborhood of $x_i$ denoted as $\mathcal{N}_i^o$, is the k-nearest patients of $x_i$ with the same label. 2) The heterogeneous neighborhood of $x_i$, denoted as $\mathcal{N}_i^e$, is the k-nearest patients of $x_i$ with different labels.

Based on these two neighborhoods, we define the local compactness of point $x_i$ as $$C_i = \sum_{x_j \in \mathcal{N}_i^o} d_m^2(x_i, x_j) \quad (2)$$

and the local scatterness of point $x_i$ as $$S_i = \sum_{x_k \in \mathcal{N}_i^e} d_m^2(x_i, x_k) \qquad (3)$$

The discriminability of the distance metric $d_m$ is defined as $$\mathcal{J} = \frac{\sum_i C_i}{\sum_i S_i} = \frac{\sum_i \sum_{x_j \in \mathcal{N}_i^o} (x_i - x_j)^T P(x_i - x_j)}{\sum_i \sum_{x_k \in \mathcal{N}_i^e} (x_i - x_k)^T P(x_i - x_k)} \qquad (4)$$

The goal is to find a P that minimizes $\mathcal{J}$, which is equivalent to minimizing the local compactness and maximizing the local scatterness simultaneously. In contrast with linear discriminant analysis, which seeks a discriminant subspace in a global sense, the localized supervised metric aims to learn a distance metric with enhanced local discriminability. To minimize $\mathcal{J}$, we formulate the problem as a trace ratio minimization problem and use the decomposed Newton's method to find the solution.

Since P is a low-rank positive semi-definite matrix, we can decompose the precision matrix as $P=WW^T$, where $W \in \mathfrak{R}^{N \times d}$ and $d \leq N$. The distance metric can be rewritten as $d_m(x_i,x_j)=\|W^T x_i - W^T x_j\|$. Therefore, the distance metric is equivalent to Euclidean distance over the low-dimensional projection $W^T x$.

Model learning module 128 takes as input the patient features 122 for patients x, physician features for physicians y, patient-to-physician features for pairs (x,y). The model learning module 128 outputs information employed in creating or updating the outcome prediction model 130. The outcome prediction model 130 is employed to determine a predicted outcome (either actual outcome, or probability of a good outcome). The outcome prediction model 130 is created or updated by the model learning module 128 using one or more of logistic regression, ordinal regression, or other predictive modeling methods including boosting, support vector machines (SVM), neural networks (NN) methods.

Outcome computation module 116 generates outcome measures 118 which are employed by patient-to-physician feature extraction module 114 and model learning module 128. Outcome measures 118 are determined based on medical literature and other external sources of information. Outcome measures 118 are computed using the available medical data. The medical data may include procedural data, e.g., emergency room visits, hospital visits, etc.; diagnostic data, e.g., severity change, known complications, etc.; physiological data, e.g., changes in lab test results. The outcome measures 118 provide usable information that can be applied to assist in making predictions of patient outcomes.

It should be understood that the feature extraction and outcome computations (blocks 110, 114, 116 and 120) are usually performed at training time or upon enrollment of a new patient or physician. As such, blocks 110, 114, 116 and 120 may be omitted from an application or software package and features may be updated to the application or software package as needed. In addition, model learning 128 may be employed during training to create models 130, and employed when updates are needed.

As an example, we want to develop a model to predict how well a physician will be able to manage any diabetes patient in terms of Hemoglobin A1C control. In the model training phase, historical records regarding the group of available physicians and the patients they have treated in the past are collected (blocks 102, 104, 106, 108). The outcomes for these past treatments are computed 116 to provide outcome measures 118. The patient feature extraction 110 extracts relevant medical data for diabetes patients, including past lab tests, age, gender, location, etc. Physician feature extraction module 120 extracts physician information, including location, practice patterns for hemoglobin A1C control (e.g., medications prescribed, tests ordered), etc. Patient-to-physician feature extraction module 114 computes feature vectors (centroids) representing each physician's "successfully controlled" and "failing" populations based on past records. The resulting patient features 112, physician features 126 and patient-to-physician features 124, along with the outcome measures 118 are input to the model learning module 128, which trains an outcome predictive model 130.

Given a current patient 112, the patient features of this patient are computed using patient feature extraction module 110, the patient-to-physician features of this patient are computed using module 114, by computing the distance between the patient features of the current patient 112, and the pre-computed centroids of each physician. These features, along with pre-computed physician features, are then input to outcome prediction model 130, which produces a predicted likelihood of successful hemoglobin A1C control for the current patient by each one of the available physicians. The model training phase can be re-run on a regular basis as more data becomes available to incorporate any changes in physician care patterns and outcomes.

As another example, a patient P has a chronic condition C. The patient P contracts a disease B. P is now looking for a physician or healthcare professional that can provide treatment. P's profile 102, medical records 104 and administrative records 106 are input into system 100, are already stored in memory within the system 100, or are accessed from a database or other eternal source. Patient feature extraction module 110 extracts the relevant medical data for the patient including the combination of ailments C and B, the patient's age, location and any other pertinent information. Based on P's extracted features 122, extracted features from other patients (outcome measures 118 and/or patient-physician features 124), and physician features 126, a model (130) is built or updated for P. The model 130 includes data for each of a plurality of physicians and outcomes for patients with the ailment combination B and C for someone fitting P's profile. In one embodiment, the model 130 computes scores for each physician and predicts a prognosis for P for each physician. The output provides guidance for the patient P to select a physician with a best predicted outcome for her particular ailments (B and C) at the present time. The model 130 may also be employed to predict outcomes over time with respect to different treatment regimens with different healthcare professionals.

The prediction model 130 provides a procedure that accepts as input the set of features, and returns a continuous or categorical outcome. This procedure can be flat (e.g. a single weight vector to multiply the features), or a more composite one (e.g. hierarchically combining subsets of the features, and combining their outcome into the final outcome, a decision tree, etc.). The models can be generated by various machine learning algorithms, e.g., logistic regression, decision trees, or with ensemble methods (e.g. stacking) combining one or more such algorithms over the set of features.

For the training phase of the system, patients are selected based on their medical condition, and the pre- and post-treatment timeframes for data available for them. Physicians are selected based on the number of patients associated with the physicians having a related condition.

Figure 2:
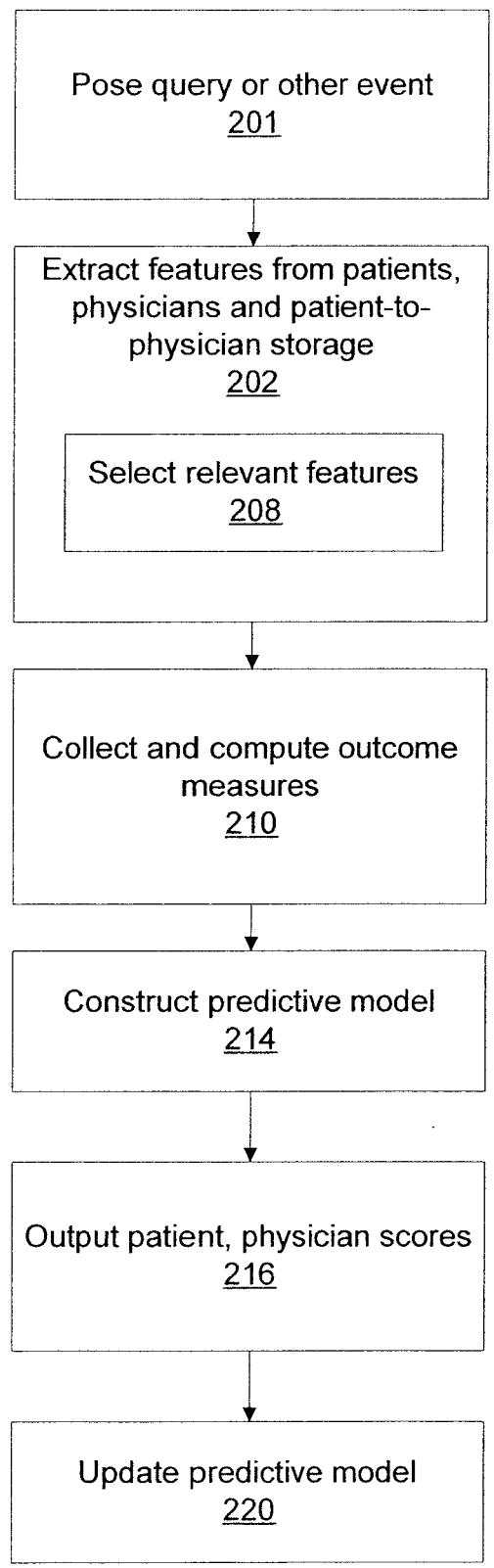
FIG. 2 is a block/flow diagram showing a system/method for generating physician outcome scores for selecting a physician in accordance with another embodiment.

Referring to FIG. 2, a recommendation system/method in shown in accordance with the present principles. FIG. 2 shows both training steps (e.g., blocks 202, 210, 214, and 220) and physician referral steps (e.g., blocks 201, 202, 210, 216 and 220) together. Some functions and steps are employed in training, retraining and implementation of the systems and methods. However, it should be understood that training may be performed separately and the system may be intermittently updated, as needed. In block 201, a conditional query is posed to output patient, physician pair scores for a current patient and a plurality of physicians to select a physician based upon the pair scores. In block 202, features are extracted. The features are extracted for a current patient, and depending on how its models are trained other features may also be extracted. In one embodiment, patient features, physician features and patient-to-physician features are extracted from medically related records for a current patient, a group of patients and one or more physicians. Patient features of a current patient may be extracted from a patient profile including biographical patient data, and/or from physician profiles including medical practice information and patient treatment information. Patient-to-physician features may be extracted which include outcomes of similar patients treated by the one or more physicians. In block 208, extracting includes selecting relevant features. These features may be limited to a query at hand or automatically be selected based upon the state of a current patient, or a determination or need or relevance.

In block 210, outcome measures are made available. The outcome measures may be collected and computed from related health care data at training time. The outcome measures may include statistics collected from medical literature or other sources for similar patients. This provides information about outcomes in different geographical regions, for different treatment options, over a larger population of similarly situated patients, etc.

In block 214, at least one predictive model is constructed from the features and outcome measures to predict a future outcome for a patient, physician pair. The predictive models are employed to determine possible outcomes for the current patient with different physicians, different treatment options, different treatment timelines, etc. of combinations thereof. In block 216, patient, physician pair scores are output for a current patient and a plurality of physicians to select a physician based upon the pair scores. This output may be responsive to the query, based upon entered patient data or other triggering event. In block 220, a current patient's information is added to update the at least one predictive model. Other information may be used to update the model as well.

In block 216, outcome scores are provided for each of a plurality of physicians (or other healthcare professionals). In one embodiment, the scores are based upon the extracted features to provide a best suited healthcare professional for the current patient under the current conditions (ailments, etc.). In another embodiment, a best treatment plan may be output that provided a best physician for different segments of the patient treatment, for example, radiation with doctor 1, chemotherapy with doctor 2, etc. The models may be adjusted to permit other outputs as well.

Figure 3:
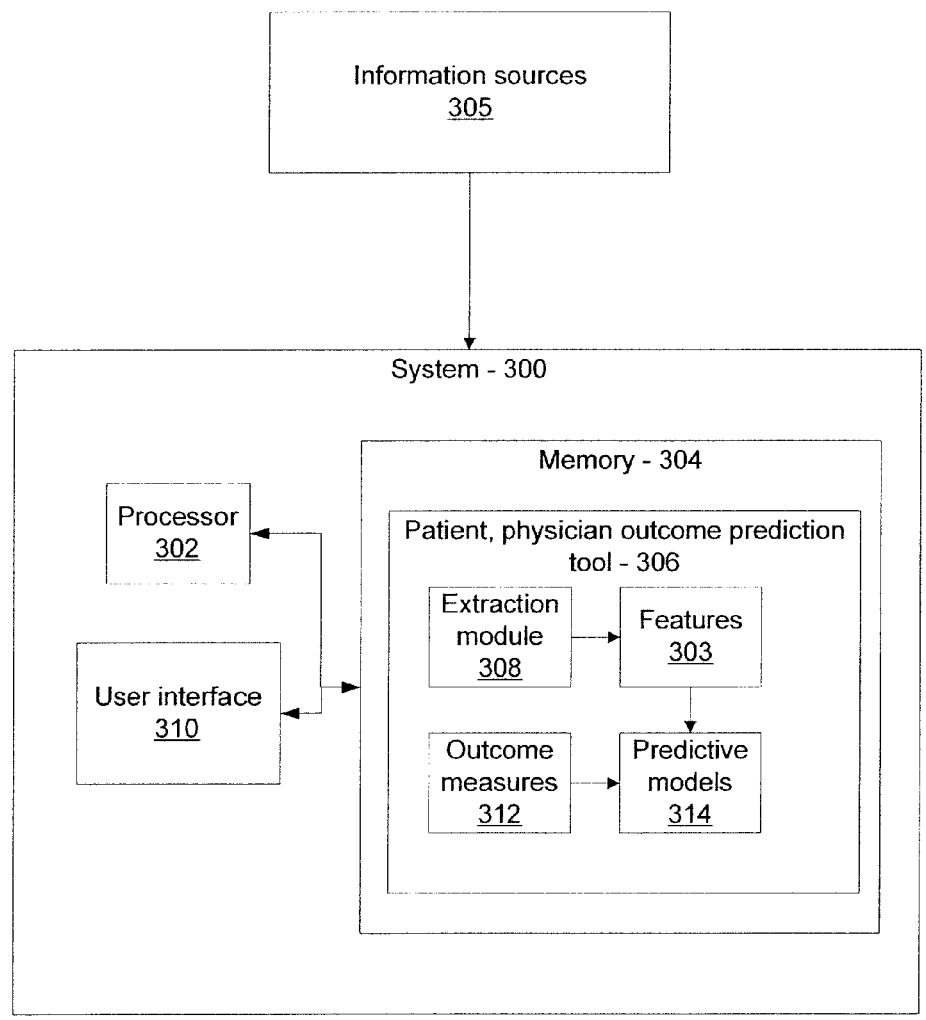
FIG. 3 is a block diagram showing a system for selecting a physician in accordance with another embodiment.

Referring to FIG. 3, a system 300 for recommending a healthcare professional is shown in accordance with one illustrative embodiment. System 300 includes at least one processor 302 and a memory 304 coupled to the processor 302. The memory 304 stores patient profiles, medical records, administrative records, healthcare professional profiles, outcome prediction data, etc. Memory 304 may be local to the system or may be distributed or accessed remotely from one or more sources 305. Memory 304 includes a patient, physician pair outcome prediction tool 306. The tool 306 includes an extraction module 308 configured to extract patient features, physician features and patient-to-physician features from medically related records for a current patient, a group of patients and one or more physicians (e.g., generally referred to as features 303 stored in memory 304). The features extracted may depend on a query or input to the system 300. The system 300 includes a user interface 310 configured to permit a user to enter information into the system 300 and to output a recommendation or referral. Interface 310 may include a mouse, keyboard, display, etc.

Memory 304 or other systems may store outcome measures 312 collected by parsing health care data from medical literature or other sources related to a current query. The outcome measures 312 include statistics from medical literature for similar patients. One or more predictive models 314 are constructed from the features 303 and outcome measures 312 to predict a future outcome for a patient, physician pair. These models 314 may be constructed or stored from previous model learning efforts.

In one embodiment, the extraction module 308 extracts patient features of a current patient from a patient profile including biographical patient data. Physician features from physician profiles may be stored or extracted. Physician features may include medical practice information and patient treatment information. Patient-to-physician features may be stored or extracted and may include outcomes of similar patients treated by the one or more physicians.

The predictive model 314 outputs patient, physician pair scores for a current patient and a plurality of physicians—to select a physician based upon the pair scores. The patient, physician pair scores may be responsive to a conditional query or other trigger. The predictive model 314 is preferably updated by adding a current patient's information or other updated patient information as it is discovered.

Having described preferred embodiments of systems and methods for outcome based referral using healthcare data of patient and physician populations (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A recommendation method, comprising:
   extracting patient features for a current patient to generate a representation of the current patient, wherein the patient features include data from at least one of patient profile records and medical records of the current patient;
   comparing the patient features for the current patient to physician features of one or more physicians and patient-to-physician features of a group of patients from medically related records;
   comparing outcome measures associated with physicians related to a current query; and
   predicting a future outcome, using a computer device, for patient, physician pairs for the current patient based upon at least one predictive model constructed from the features and outcome measures to output.

2. The method as recited in claim 1, wherein extracting patient features includes extracting patient features of a current patient from a patient profile including biographical patient data.

3. The method as recited in claim 1, wherein extracting patient features includes selecting relevant features, and the patient features are represented by one or more N-dimensional feature vectors.

4. The method as recited in claim 1, further comprising extracting physician features from physician profiles including medical practice information and patient treatment information, wherein the physician features are represented by one or more N-dimensional feature vectors.

5. The method as recited in claim 1, further comprising extracting patient-to-physician features including outcomes of similar patients treated by the one or more physicians.

6. The method as recited in claim 1, wherein comparing outcome measures includes collecting statistics from medical literature for similar patients.

7. The method as recited in claim 1, further comprising: outputting patient, physician pair scores for a current patient and a plurality of physicians to select a physician based upon the pair scores.

8. The method as recited in claim 1, further comprising: posing a conditional query to output patient, physician pair scores for a current patient and a plurality of physicians to select a physician based upon the pair scores.

9. The method as recited in claim 1, further comprising: adding a current patient's information to update the at least one predictive model.

10. A non-transitory computer readable storage medium comprising a computer readable program, wherein the computer readable program when executed on a computer causes the computer to perform the steps of:
   extracting patient features for a current patient to generate a representation of the current patient, wherein the patient features include data from at least one of patient profile records and medical records of the current patient;
   comparing the patient features for the current patient to physician features of one or more physicians and patient-to-physician features of a group of patients from medically related records;
   comparing outcome measures associated with physicians related to a current query; and
   predicting a future outcome for patient, physician pairs for the current patient based upon at least one predictive model constructed from the features and outcome measures to output.

11. The computer readable storage medium as recited in claim 10, wherein extracting patient features includes extracting patient features of a current patient from a patient profile including biographical patient data.

12. The computer readable storage medium as recited in claim 10, wherein extracting patient features includes selecting relevant features, and the patient features are represented by one or more N-dimensional feature vectors.

13. The computer readable storage medium as recited in claim 10, further comprising extracting physician features from physician profiles including medical practice information and patient treatment information, wherein the physician features are represented by one or more N-dimensional feature vectors.

14. The computer readable storage medium as recited in claim 10, further comprising extracting patient-to-physician features including outcomes of similar patients treated by the one or more physicians.

15. The computer readable storage medium as recited in claim 10, wherein comparing outcome measures includes collecting statistics from medical literature for similar patients.

16. The computer readable storage medium as recited in claim 10, further comprising: outputting patient, physician pair scores for a current patient and a plurality of physicians to select a physician based upon the pair scores.

17. The computer readable storage medium as recited in claim 10, further comprising: posing a conditional query to output patient, physician pair scores for a current patient and a plurality of physicians to select a physician based upon the pair scores.

18. The computer readable storage medium as recited in claim 10, further comprising: adding a current patient's information to update the at least one predictive model.

19. A system, comprising:
   a processor,
   memory coupled to the processor, the memory storing a patient, physician pair outcome prediction tool, the tool comprising:
   an extraction module configured to store patient features, physician features and patient-to-physician features from medically related records for a current patient, a group of patients and one or more physicians, wherein the patient features include data from at least one of patient profile records and medical records of the current patient;
   outcome measures stored from health care data related to a current query; and
   at least one predictive model constructed from the features and outcome measures to predict a future outcome for a patient, physician pair.

20. The system as recited in claim 19, wherein the extraction module extracts patient features of a current patient from a patient profile including biographical patient data; extracts physician features from physician profiles including medical practice information and patient treatment information, wherein the physician features are represented by one or more N-dimensional feature vectors; and extracts patient-to-physician features including outcomes of similar patients treated by the one or more physicians.

21. The system as recited in claim 19, wherein the outcome measures include statistics from medical literature for similar patients.

22. The system as recited in claim 19, wherein the at least one predictive model outputs patient, physician pair scores for a current patient and a plurality of physicians to select a physician based upon the pair scores.

23. The system as recited in claim 19, wherein the at least one predictive model outputs patient, physician pair scores, responsive to a conditional query, for a current patient and a plurality of physicians to select a physician based upon the pair scores.

24. The system as recited in claim 19, wherein the at least one predictive model is updated by adding a current patient's information.

25. The system as recited in claim 19, further comprising a user interface configured to pose a query for determining a physician.

* * * * *